United States Patent [19]
Slattery

[11] Patent Number: 5,942,274
[45] Date of Patent: *Aug. 24, 1999

[54] RECOMBINANT HUMAN MILK PROTEINS IN INFANT FORMULAS

[76] Inventor: Charles W. Slattery, 11403 Golden Gate Dr., Yucaipa, Calif. 92399

[*] Notice: This patent is subject to a terminal disclaimer.

[21] Appl. No.: 09/100,377

[22] Filed: Jun. 19, 1998

Related U.S. Application Data

[63] Continuation of application No. 07/453,779, Dec. 20, 1989, Pat. No. 5,795,611.

[51] Int. Cl.$^6$ ........................................................ A23C 9/00
[52] U.S. Cl. ........................... 426/580; 426/585; 426/801; 435/69.1
[58] Field of Search ..................................... 426/580, 585, 426/801, 656; 435/69.1

[56] References Cited

U.S. PATENT DOCUMENTS

| | | |
|---|---|---|
| 4,544,633 | 10/1985 | Gil et al. . |
| 4,753,926 | 6/1988 | Lucas et al. . |
| 4,935,354 | 6/1990 | Hayenga et al. . |
| 4,963,384 | 10/1990 | Heine et al. . |
| 5,795,611 | 8/1998 | Slattery .................................. 426/580 |

OTHER PUBLICATIONS

Am. Acad. of Pediatrics Comm. on Nutrition, *Pediatrics* 72, 359–363 (1983).
Hambraeus, et al, "Food and Immunology" pp. 116–124 Eds. L. Hambraeus, L.A. Hanson and H. McFarlane) Almquist and Wiksell (1977).
Brock, T.D., et al. "Biology of Microorganisms" pp. 379–400, Prentice–Hall, inc., New Jersey (1984).
Findlay, J.B.C. and Brew K., "The Complete Amino–Acid Sequence of Human Lactalbumin". *European Journal of Biochemistry*, 27, pp. 64–85 (1972).
Newport, M.J., et al., *Pediatric Res.* 18, 658–662 (1984).
Axelsson, et al, *Acta Pediatrica* Scand. 75, 1702–707 (1986).
Sood, et al., *Arch. Biochem. Biophys* 264, 574–583 (1988).
Chirgwin, et al., *Biochemistry* 18, 5294–5299 (1979).
Gubler, et al., *Gene* 25, 263–269 (1983).
Menon, R.S., et al., *J. Cell Biol.* 107, 523a (1989), *Nucl. Acids Res.* 17, 2869 (1989).
Findlay et al., *Eur. J. Biochem.* 27 65–86 (1972).
Greenberg, et al., *J. Biol. Chem.* 259, 5132–5138 (1984).
Kang, et al., *J. Dairy Sci.* 71, 29–40 (1988).
Amann, et al., *Gene* 25, 167–178 (1983).
Messing, *Methods Enzymol* 101, 20–79 (1983).
Zsebo, et al., *J. Biol. Chem.*, 261, 5858–5865 (1986).
Shewale, et al., *J. Biol. Chem.*, 259, 4947–4956 (1984).
Brew, et al., *J. Biol. Chem.*, 248, 4739–4742 (1973).
Sood, et al., *Arch Biochem. Biophys.*, 242, 355–364 (1985).
V.S. Packard, "Human Milk and Infant Formula", pp. 147–154, Academic Press (1982).
R. Hawkes, *Anal. Biochem.*, 123, 143–146 (1982).

*Primary Examiner*—Leslie Wong
*Attorney, Agent, or Firm*—Knobbe, Martens, Olson & Bear, LLP

[57] ABSTRACT

A human infant formula sufficient to meet the nutritional requirements of a human infant, comprising proteins having substantially the same amino acid sequence and biological properties as human alpha-lactalbumin and human beta-casein. The proteins may be produced from microorganisms, particularly *E. coli*. A recombinant DNA segment comprising a human milk protein encoding gene; a promoter sequence directing the transcription of the gene, where the promoter sequence is different from the promoter sequence for the gene in the human organism; and a terminator site for the human milk protein encoding gene. A microorganism containing a recombinant DNA segment comprising a human milk protein encoding gene; a promoter sequence directing the transcription of the gene; and a terminator site for the gene.

11 Claims, No Drawings

RECOMBINANT HUMAN MILK PROTEINS IN INFANT FORMULAS

This application is a continuation of prior application U.S. Ser. No. 07/453,779, filed Dec. 20, 1989, now U.S. Pat. No. 5,795,611.

BACKGROUND OF THE INVENTION

For healthy human mothers otherwise not exposed to contaminating environmental pollutants or toxins, mother's milk constitutes the best food for full-term, vigorous human infants. Unfortunately, most infants are not breast fed at all, or if breast fed, not for an adequate period of time. In the United States and other developed nations, surveys show that even during a time when the percentage of mothers choosing to breast-feed rose from 25% to 35%, less than one-tenth of those mothers continued to breast-feed beyond three months (U.S. Department of Health, Education and Welfare (1979), "Trends in Breast-Feeding Among American Mothers", DHEW Publication No. (PHS) 79-1979, National Center for Health Statistics, Hyattsville, Md.). If second births are considered, the percentage of breast-fed infants in all categories is reduced even further. Consequently, a large majority of American mothers still rely on bottle feeding, either of infant formula or some other substitute for breast milk. Presently, commercially available human infant formula used to replace mother's milk is based primarily upon the protein constituents of cow's milk. These infant formula compositions have led to difficulties in terms of nutrient balance, bioavailability of nutrients and sensitivity of human infants to non-human/animal protein. Specifically, allergic reactions to the non-human animal protein used with these infant formulas caused a change in the protein component of the commercially available formula to soy-protein based formulas, although many infants that are allergic to cow's milk are also allergic to soy-based milks (Am. Acad. of Pediatrics Comm. on Nutrition, Pediatrics, 72, 359–363 (1983)).

Additionally, many of the problems with the use of cow's milk protein are associated with difficulties in digestibility because of bovine casein content and structure (L. Hambraeus, E. Forsum and B. Lonnerdal. In: "Food and Immunology", pp 116–124 (Eds. L. Hambraeus, L. A. Hanson and H. McFarlane) Almquist and Wiksell (1977)).

This has led to the production of infant formulas which contain a greater proportion of whey protein, since it is more readily digested by human infants (M. J. Newport and M. J. Henschel, *Pediatric Res.*, 18, 658–662 (1984)), and little or no bovine casein. However, the major protein in whey of cow's milk is beta-lactoglobulin. This protein is essentially absent from human milk and has been determined to be one of the main causes of cow's milk allergy in infants. (I. Axelsson, I. Jakobsson, T. Lindberg and B. Benedikstsson, *Acta Pediatrica Scand.*, 75, 702–707 (1986)). The extent of the problems with allergies to formulas based on cow's milk may be appreciated from the fact that soy-based formulas now comprise a large portion of the human infant formula market in the United States.

Soy-protein formulas, although different in carbohydrate and protein source, are similar in composition to cow's milk-protein formulas following the American Academy of Pediatrics, Committee on Nutrition recommendations for nutrient levels in infant formulas. Differences include a slightly higher protein level and slightly lower carbohydrate content. The protein source is generally soy-protein; the fat is a blend of vegetable oils; and the source of carbohydrate is usually sucrose, corn syrup solids, or a mixture of both. However, the use of soy formulas tends to raise serum alkaline phosphatase and blood urea levels in infants in addition to causing the allergic and digestibility problems encountered with the use of bovine-based protein infant formulas.

Therefore, there exists a present need for a manufacturable human infant formula which comprises a digestible, non-allergenic protein source. Recent research on the activity of human beta-casein has shown that the non-phosphorylated form acts much like human casein in that it precipitates at the calcium ion levels found in mother's milk and binds to the insoluble calcium phosphate just as phosphorylated caseins do (S. M. Sood, P. Chang and C. W. Slattery, *Arch. Biochem. Biophys.*, 264, 574–583 (1988)).

Therefore, proteins which have not been modified post-ribosomally by phosphorylation may be used along with carrageenan to replace the stabilization effects of kappa-casein in infant formula. Thus, providing human infant formulas constituted with purified non-phosphorylated human milk proteins produced by microorganisms (e.g., *E. coli* or *S. cerevisiae*) provides a unique answer in solving the inherent digestibility and allergenic problems associated with the use of non-human proteins in human infant formula compositions.

Recombinant DNA techniques may be used to clone cells producing large quantities of the necessary human proteins which may be purified and then combined with carbohydrates, lipids, minerals and sources of non-protein nitrogen to give a simulated human mother's milk formula that does not exhibit the allergenic properties associated with formulas based on cow or other foreign protein. A formula that is nutritionally adequate may be prepared by using only two human proteins: alpha-lactalbumin, which is the major protein of human whey; and beta-casein, the major protein of the casein micelle fraction of human milk. There are a variety of methods for producing these proteins. Representative procedures will be described herein.

SUMMARY OF THE INVENTION

Thus, in accordance with one aspect of the present invention, there is provided a human infant formula of the type comprising proteins, lipids from vegetable sources, vitamins and minerals, with the improvement comprising: providing proteins in the form of proteins having substantially the same amino acid sequence and biological properties as human alpha-lactalbumin and human beta-casein. Particularly, the proteins may be produced from microorganisms; most particularly, *E. coli*.

In accordance with another aspect of the present invention, there is provided a human infant formula comprising proteins, lipids from vegetable sources, vitamins, and minerals sufficient to meet the nutritional requirements of a human infant, in which the proteins have substantially the same amino acid sequence and biological properties as human alpha-lactalbumin and human beta-casein.

In accordance with yet another aspect of the present invention, there is provided a method to meet the nutritional requirements of human infants, comprising the steps of: providing a human infant formula comprising proteins, lipids from vegetable sources, vitamins, and minerals, in which the proteins are human alpha-lactalbumin and human beta-casein which are produced by microorganisms; and, feeding an infant the human infant formula.

In accordance with yet another aspect of the present invention, there is provided a plant, an animal or a microorganism, comprising a recombinant DNA segment comprising at least one promoted heterologous gene coding for the amino acid sequence of a protein found in human milk, the amino acid sequence preferably substantially that of human alpha-lactalbumin and/or human beta-casein.

In accordance with another aspect of the present invention, there is provided a recombinant DNA segment comprising: a human alpha-lactalbumin and/or human beta-casein encoding gene; a promoter sequence directing the transcription of the gene; and a terminator site for the gene. In a preferred embodiment, there is provided a recombinant DNA vector containing the recombinant DNA segment comprising the human alpha-lactalbumin and/or human beta-casein encoding gene.

In accordance with yet another aspect of the present invention, there is provided a method for inducing a plant, an animal or a microorganism to produce proteins having substantially the same amino acid sequence as proteins found in human milk, comprising the steps of: inserting at least one promoted, heterologous, expressible recombinant DNA segment coding for the amino acid sequence of the protein into a recombinant DNA vector, and expressing the expressible recombinant DNA segment in a microorganism.

In accordance with still another embodiment of the present invention, there is provided a method for producing a human infant formula which contains proteins substantially comprising the amino acid sequence of human milk proteins, lipids derived from a non-human source, vitamins, minerals and other nutrients essential to meet the nutritional requirements of the human infant, comprising the steps of: inserting at least one promoted, heterologous, expressible recombinant DNA segment coding for the amino acid sequence of the human milk proteins into a vector to produce a transforming vector; transforming a microorganism by use of the transforming vector; obtaining expression of the human milk proteins by the transformed microorganism; harvesting and purifying the human milk proteins expressed by the microorganism; and formulating a human infant formula with the proteins.

DETAILED DESCRIPTION OF THE INVENTION

Preparation of a cDNA Library

To produce human alpha-lactalbumin and beta-casein in microorganisms, epithelial cells from the human mammary gland must be obtained which may be treated with hormones, such as prolactin, to induce protein synthesis. Appropriate cell lines are commercially available from a variety of sources, such as the Michigan Cancer Foundation. From the prolactin treated cells, mRNA may be obtained by isolating total RNA (J. M. Chirgwin, A. E. Przybyla, R. J. MacDonald and W. J. Rutter, *Biochemistry*, 18, 5294–5299 (1979)), and then the poly (A)+RNA fraction (H. Avis and P. Leder, *Proc. Natl. Acad. Sci.*, 69, 1408–1412 (1972)). Single and double stranded cDNA are prepared from this (U. Gubler and B. J. Hoffman, *Gene*, 25, 263–269 (1983)), followed by ligation and transfection to construct the library, ("Current Protocols in Molecular Biology", F. M. Ausubel, R. Brent, R. E. Kingston, D. D. Moore, J. G. Seidman, J. A. Smith and K. Struhl, editors, John Wiley and Sons, New York (1987)) with subsequent isolation of the particular genes.

As an alternative procedure, a commercial cDNA library (HZ1037) is available from Clontech Labs, Inc. (Palo Alto, Calif.), prepared from human mammary tissue cells from a woman 8 months pregnant. Such a cDNA library has been used (Menon and Ham, *J. Cell Biol.*, 107, 523a (1989); S. Menon and R. G. Ham, *Nucl. Acids Res.*, 17, 2869 (1989)) to prepare, clone and sequence human beta-casein cDNA.

Gene Synthesis

The complete amino acid sequence is known for both alpha-lactalbumin and beta-casein:

The Amino-Acid Sequence of Human α-Lactalbumin

```
             1                                    10
Lys-Gln-Phe-Thr-Lys-Cys-Glu-Leu-Ser-Gln-Leu-Leu-Lys-Asp-

20
Ile-Asp-Gly-Tyr-Gly-Gly-Ile-Ala-Leu-Pro-Glu-Leu-Ile-Cys- 30                                          40
Thr-Met-Phe-His-Thr-Ser-Gly-Tyr-Asp-Thr-Gln-Ala-Ile-Val-

50
Glu-Asn-Asp-Gln-Ser-Thr-Glu-Tyr-Gly-Leu-Phe-Gln-Ile-Ser- 60                                       70
Asn-Lys-Leu-Trp-Cys-Lys-Ser-Ser-Gln-Val-Pro-Gln-Ser-Arg-

80
Asn-Ile-Cys-Asp-Ile-Ser-Cys-Asp-Lys-Phe-Leu-Asn-Asp-Asn-

90
Ile-Thr-Asn-Asn-Ile-Met-Cys-Ala-Lys-Lys-Ile-Leu-Asp-Ile- 100                                         110
Lys-Gly-Ile-Asn-Tyr-Trp-Leu-Ala-His-Lys-Ala-Leu-Cys-Thr-

120
Glu-Lys-Leu-Glu-Gln-Trp-Leu-Cys-Glu-Lys-Leu
```

(J. B. C. Findlay and K. Brew. Eur.J.Biochem. 27, 65–86 (1972))

The Amino-Acid Sequence of Human β-Casein

```
      1                                              10
```

-continued

```
Arg-Glu-Thr-Ile-Glu-Ser-Leu-Ser-Ser-Ser-Glu-Glu-Ser-Ile-
                    20
Pro-Glu-Tyr-Lys-Gln-Lys-Val-Glu-Lys-Val-Lys-His-Glu-Asp-
       30                              40
Gln-Gln-Gln-Gly-Thr-Asp-Gln-His-Gln-Asp-Lys-Ile-Tyr-Pro-
                       50
Ser-Phe-Gln-Pro-Gln-Pro-Leu-Ile-Tyr-Pro-Phe-Val-Glu-Pro-
              60                              70
Ile-Pro-Tyr-Gly-Phe-Leu-Pro-Gln-Asn-Ile-Leu-Pro-Leu-Ala-
                           80
Gln-Pro-Ala-Val-Val-Leu-Pro-Val-Pro-Gln-Pro-Glu-Ile-Met-
                  90
Glu-Val-Pro-Lys-Ala-Lys-Asp-Thr-Val-Tyr-Thr-Lys-Gly-Arg-
       100                              110
Val-Met-Pro-Val-Leu-Lys-Gln-Pro-Thr-Ile-Pro-Phe-Phe-Asp-
                     120
Pro-Gln-Ile-Pro-Lys-Leu-Thr-Asp-Leu-Glu-Asn-Leu-His-Leu-
              130                             140
Pro-Leu-Pro-Leu-Leu-Gln-Pro-Ser-Met-Gln-Gln-Val-Pro-Gln-
                        150
Pro-Ile-Pro-Gln-Thr-Leu-Ala-Leu-Pro-Pro-Gln-Pro-Leu-Trp-
                 160
Ser-Val-Pro-Glu-Pro-Lys-Val-Leu-Pro-Ile-Pro-Gln-Glu-Val-
       170                              180
Leu-Pro-Tyr-Pro-Val-Arg-Ala-Val-Pro-Val-Gln-Ala-Leu-Leu-
                  190
Leu-Asn-Gln-Glu-Leu-Leu-Leu-Asn-Pro-Pro-His-Gln-Ile-Tyr-
          200                                 210
Pro-Val-Pro-Glu-Pro-Ser-Thr-Thr-Glx-Ala-Asx-His-Pro-Ile-
   212
Ser-Val
```

(R. Greenberg, M. L. Groves and H. J. Dower. *J. Biol. Chem.* 259, 5132–5138 (1984))

From a knowledge of the genetic code, the sequence of the nucleic acids in the genes for these proteins may be deduced and the genes themselves produced synthetically. The length of the genes, with three nucleotides per amino acid residue, is within the capabilities of properly equipped laboratories to synthesize. In addition, the ends of the nucleotide chain comprising the gene may be designed for proper incorporation into a chosen plasmid for insertion into the microorganism and may include a start or stop codon. In the example described here, a start codon would not be needed but the sequence should end with a stop codon, such as UAA, and an unpaired sequence, complementary to the restriction endonuclease site, which is "sticky."

These genes are capable of introduction into a recipient strain by means of transformation or transfection followed by replication and amplification. The vector molecules used are plasmid DNA or DNA of temperate bacteriophages, viruses or other self-propagating DNA. Many of these methods are described in detail in the following publications:

1. Cohen, S. N.; Chang, A. C. Y; Boyer, H. W. and Helling, R. B. (1973) *Proc. Nat. Acad. Sci. USA*, 70, 3240.
2. Green, P. J.; Betlach, M. D.; Boyer, H. W. and Goodman, H. N. (1974) *Methods in Molecular Biology*, 7, 87.
3. Tanaka, T. and Weisblum, B. (1975) *J.Bacteriol*, 121, 354.
4. Clarke, L. and Carbon, J. (1975) *Proc. Nat. Acad. Sci. USA*, 72, 4361.
5. Bolivar, F.; Rodrigues, R. L.; Green, P. J.; Betlach, M. C.; Heyneker, H. L. and Boyer, H. W. (1977) *Gene*, 2, 95.
6. Kozlov, J. I.; Kalinina, N. A.; Gening, L. V.; Rebentish, B. A.; Strongin, A. J.; Bogush, V. G. and Debabov, V. G. (1977) *Molec. Gen. Genetics*, 150, 211.

Introduction of Promoter Sequences

Different organisms, of course, recognize different promoter sequences. Therefore, various new promoter sequences appropriate for different host bacteria or yeasts may be introduced onto the genes coding for alpha-lactalbumin and/or beta-casein into a unique site in the vector and for introducing the assembled DNA sequence into a variety of cloning vectors. Alternatively, the new promoter may be introduced via a particular restriction endonuclease site in the plasmid which allows for insertion of the sequence into the genome of any of a variety of appropriate host bacteria or yeast the genes calling for human alpha-lactalbumin or beta-casein. The following are a representative list of hosts and promoters:

TABLE 1

| Host Bacterium or Yeast | Promoter | Reference |
|---|---|---|
| Corynebacterium diptheriae | Corynebacteriophage Beta toxin gene | Tweten, R. K. and Collier, R. J. J. Bacteriol. (1983) 156, 680–685 |
| | Corynebacteriophage Beta constitutive toxin gene (eg. tox-201) | Welkos, S. L. and Holmes, R. K. J. Virol. (1981) 37, 946–954 |
| | Corynebacteriophage Gamma c toxin gene | Michel, J. L., et al. J. Virol. (1982) 42, 510–519 |
| Bacillus subtilis | Sporulation gene spo 11A | Ydukin, M. D., et al. J. Gen. Microbiol. (1985) 131, 959–962 |
| | dnaE gene | Wang, L. F., et al. J. Biol. Chem. (1985) 260, 3368–3372 |
| | aspartokinase 11 gene | Bondaryk, R. P. and Paulus, H. J. Biol. Chem. (1985) 260, 585–591 |
| | Subtilisin E gene | Wang, S. L., et al. Proc. Natl. Acad. Sci. USA (1984) 81, 1184–1188 |
| | rrnB operon | Steward, G. C. and Bott, K. F. Nucl. Acids Res. (1983) 11, 6289–6300 |
| | Alpha amylase genes (amyR2, amyE) | Yamazaki, H., et al. J. Bacteriol (1983) 156, 327–337 |
| | Glutamine amido-transferase gene | Makaroff, C. A., et al. J. Biol. Chem. 258, 10586–10593 |
| Bacillus liceniformus | ermD gene | Gryczan, T., et al. Mol. Gen. Genet. (1984) 194, 349–356 |
| | sporulation gene | Ramakrishna, N., et al. Nucl. Acids Res. (1984) 12, 1779–1790 |
| | PepP gene | McLaughlin, J. R. Nucl. Acids Res. (1982) 10, 3905–3919 |
| Bacillus thuringeinsis | crystal protein gene | Wong, H. C., et al. J. Biol. Chem. (1983) 258, 1960–1967 |
| Pseudomonas sp. | Carboxypeptidase G2 gene | Minton, N. P., et al. Gene (1984) 31, 31–38 |
| Hansenula polymorpha | Methanol Oxidase gene | Ledeboer, A. M., et al. Nucl. Acids Res. (1985) 13, 3063–3082 |
| | Dihydroxyacetone Synthase gene | Janowicz, Z. A., et al. Nucl. Acids Res. (1985) 13, 1043–3062 |
| Saccharomyces cerevisiae | GAL1-GAL10 gene promoters | Johnston, M. and Davis, R. W. Mol. and Cell Biol. (1984) 4, 1440–1448 |
| | HIS3 gene promoter | Struhl, K. Proc. Natl. Acad. Sci. USA (1982) 79, 7385–7389 |
| | HIS4 gene promoter | Donahue, T. F., et al., Cell (1983) 32, 89–98 |
| | TRP5 gene promoter | Zalkin, H. and Yanofsky, C. J. Biol. Chem. (1982) 257, 1491–1500 |
| Saccharomyces | CYCc gene promoter | Russel, P. R. Nature (1983) 301, 167–169 |
| | ADH gene promoter | Russel, P. R. Nature (1983) 301, 167–169 |

Any of the promoter sequences of the genes listed in Table 1 might be used advantageously for expressing human alpha-lactalbumin or beta-casein in host organisms for which they are particularly suited.

Other microorganisms that may be used as host organisms for the present invention include bacteria, such as Clostridium sp., Serratia sp., Enterobacter sp., Salmonella sp., Klebsiella sp., Rizhobium sp., Rhodopseudomonas sp. (and other photosynthetic bacterial species), Xanthamonas sp., and the various methylotropic bacterial species, etc., and yeast such as Candida sp., Saccharomyces sp., Hansenula sp., Mucor sp. (and other filamentous fungi), etc.

Moreover, since sufficient information is now available for the introduction and expression of foreign genes into plant and animal cells and even into mature plants and animals, it is possible to insert and express these human alpha-lactalbumin and beta-casein genes into these systems.

Selection of Cloning Vector

Vectors suitable for expression of alpha-lactalbumin or beta-casein genes have different host organisms compatibilities, primarily due to their ability or inability to adapt to the DNA replication machinery of a given host organism. Consequently, in choosing a DNA vector for the expression of these genes in a given host organism, it is necessary to choose a vector capable of replication in that host organism. These DNA vectors also contain antibiotic resistance or other phenotypically selectable genes, compatible with growth and physiological properties of the host organism, in order to select, propagate, amplify and maintain the human alpha-lactalbumin or beta-casein genes. A large number of suitable plasmids are known and are readily available. For any particular organism, a person of ordinary skill in the art will recognize what plasmids are the most suitable, along with which plasmids provide suitable restriction endonuclease sites for recombinant DNA and promoter insertion.

Other Considerations

In addition to efficient promotion of transcription for expression of alpha-lactalbumin or beta-casein genes, the economical use of the cellular transcription apparatus is favored by transcription of only those sequences required for the proper efficient translation of a messenger RNA. That is, proper transcription termination, messenger RNA processing and messenger RNA translation signals must be engineered into the alpha-lactalbumin or beta-casein vectors and these signals must be compatible with the metabolic machinery of the host organism. Furthermore, it has been demonstrated that transcription termination is an important factor for maintaining high copy numbers of plasmids since transcription through the origin of replication antagonizes plasmid replication. (Adams and Hatfield (1984), *J. Biol. Chem.*, 259, 7399–7403). Examples of these signals and their proper utilization are described below:

Transcription termination.

In *E. coli*, transcription termination signals are well defined. DNA sequences containing G+C rich inverted repeats followed by 6 or more T's are known to be efficient transcription terminators. Transcription terminators in yeast are also well understood. In this case, transcription termination is coupled to polyadenylation of the terminated mRNA transcript. An example of an efficient yeast transcription terminator is that of the CYC1 locus of *Saccharomyces cerevisiae* (Zaret and Sherman (1982), *Cell*, 28, 563–573). In higher eukaryotic organisms, the mechanism of transcription termination is less well understood; however, in vitro studies (Hatfield, et al., *Mol. Cell. Biol.*, 3, 1687–1693 (1983)) have demonstrated that the bacteriophage lambda 4S terminator contains DNA sequences that are recognized by the eukaryotic RNA polymerase II, the polymerase that transcribes structural genes.

Messenger RNA processing.

Current evidence suggests that polyadenylation of prokaryotic messenger RNAs in eukaryotic organisms is important for message stability and for the transport of the mRNA from the nucleus to the cytoplasm. The signal for polyadenylation, AATAAA, has been documented for many eukaryotic genes. This sequence is found in structural genes immediately downstream of the amino acid coding region.

Messenger RNA translation.

In *E. coli*, it has been documented by Shine, J. and Delgarno, L. ((1975) *Nature*, 254, 34–38) and many other investigators that a sequence complementary to the 3'-end of the 16S ribosomal RNA is located approximately 15 nucleotides prior to the translation initiation codon on the mRNA. Translation initiation is less well understood in eukaryotes; however, as a general rule, translation appears to initiate at the first initiation codon. (Kozak (1985), *Micro. Rev.*, 47, 1–45.)

In addition to the large number of general and specific considerations set forth above, it must be recognized that the mechanisms of expression vary from organism to organism. Many of these mechanisms have been elucidated at this time. Many additional mechanisms are the subject of continuing research and will be understood more fully in the future. A person of ordinary skill in the art will understand, of course, which DNA sequences are needed to obtain expression of these human alpha-lactalbumin and beta-casein genes in any of the ever-expanding number of organisms; for instance, plants and animals, in which expression of the DNA sequence may be desired.

The preparation and expression of the vector with the genes coding for the human proteins comprising the present invention will now be described:

EXAMPLE I

*E. Coli* Expressing Human Alpha-Lactalbumin and Beta-Casein

Preparation of the Plasmid Vector

The following procedure, with some modifications, follows that used by Kang and Richardson (Y. C. Kang and T. Richardson. J. Dairy Sci. 71, 29–41 (1988)) to clone and express bovine kappa-casein in *Escherichia coli*. As a starting point, plasmid vector pKK233-2 is used. (E. Amann, J. Brosius and M. Ptashne. Gene 25, 167–178 (1983)). It contains a strong regulated trp-lac fusion promotor (trc promotor), the ribosome binding site of lactose operon, and an ATG start codon located eight nucleotides away from the ribosome binding site.

The start codon ATG is part of a site recognized by the restriction endonuclease NcoI in which the nucleotide sequences for the two DNA strands are cleaved. This leaves recessed 3' ends which are filled in by using the Klenow fragment of DNA polymerase I. (Y. C. Kang and T. Richardson. *J. Dairy Sci.*, 71, 29–41 (1988)). As long as each of the four deoxynucleotide triphosphates are supplied, the reaction fills in the empty spaces to leave blunt ends on each side of the original site, and regenerates the ATG start codon required for gene expression.

In order to prevent ligation of these ends and insert the synthetic gene into the plasmid in the proper direction, a "sticky end" needs to be formed which is complementary to the one produced on the synthetic gene. The procedure (Y. C. Kang and T. Richardson. *J. Dairy Sci.*, 71, 29–41 (1988)) is to treat the modified plasmid with the restriction endonuclease Hind III which cleaves the plasmid site to give an unpaired AGCT sequence.

In this case, because Hind III recognizes a palindromic sequence, the complementary end produced on the synthetic gene has the same AGCT sequence. The gene and the plasmid may then be mixed under the proper conditions for insertion and joined together by the action of T4 ligase (Y. C. Kang and T. Richardson. *J. Dairy Sci.*, 71, 29–41 (1988)) to finally yield a transforming plasmid vector. The blunt end of the synthetic gene which codes for the N-terminal amino acid residue will ligate to the blunt end of the plasmid containing the ribosome binding site and the start codon while the sticky end following the stop codon will ligate to the sticky end of the Hind III site in the plasmid.

Transformation and Cloning

The ligation mixture is then used to transform competent cells of *E. coli* JM105. (J. Messing. *Methods Enzymol.*, 101, 20–78 (1983)). The cells are then grown on plates in media containing LB-ampicillin. Since the PKK233-2 plasmid has a gene coding for resistance to ampicillin, only those cells which have incorporated the plasmid will survive. The surviving colonies are then transferred to LB-ampicillin broth for growth and checked for the expression of the desired protein, either alpha-lactalbumin or beta-casein, using antibodies. Those colonies that express the desired proteins are then grown and the expected proteins are isolated by any of a number of conventional methods such as harvesting the cells and isolating the protein from cell extract; or by collecting secreted protein in growth medium. (R. Hawkes. *Anal. Biochem.*, 123, 143–146 (1982)). A large percentage of the protein produced by the *E. coli* cells prepared in this manner is either alpha-lactalbumin or beta-casein.

EXAMPLE II

Human Milk Protein Production in Yeast

In a manner similar to that described in Example I for *E. coli*, plasmids are constructed, for introduction into *S. cerevisiae*, which have sections for autonomous extrachromosomal replication, ampicillin resistance and binding to the spindle apparatus during mitosis as well as a section containing a portion of a bacterial plasmid that directs expression of foreign protein ("The Molecular Biology of the Yeast Saccharomyces: Life Cycle and Inheritance" (1981) and "The Molecular Biology of the Yeast Saccharomyces: Metabolism and Gene Expression" (1982), J. N. Strathern, E. W. Jones and J. R. Broach, editors, Cold Spring Harbor Laboratory, Cold Spring Harbor, N.Y.). Proteins are not only expressed but are also believed to be secreted (K. M. Zsebo, H. -S. Lu, J. C. Fieschko, L. Goldstein, J. David, K. Duker, S. V. Suggs, P. -A Lai and G. A. Bitter, *J. Biol. Chem.* 261, 5858–5865 (1986)).

Protein Purification

The production of large amounts of single proteins by cells simplifies the purification procedures. A two-step procedure separates the alpha-lactalbumin from cytosol proteins by ion exchange chromatography with DEAE-cellulose and gel filtration with Sephadex G-75. (J. G. Shewale, S. K. Sinha and K. Brew. *J. Biol. Chem.*, 259, 4947–4956 (1984)). Protein is assayed by its ability to promote lactose synthesis with galactosyl transferase. (K. Brew, H. M. Steinman and R. L. Hill. *J. Biol. Chem.*, 248, 4739–4742 (1973)). Similarly, beta-casein is separated by isoelectric precipitation, ion-exchange chromatography and gel filtration. (S. M. Sood, P. Chang and C. W. Slattery. Arch Biochem. Biophys. 242, 355–364 (1985)). Purified proteins may be freeze-dried for convenience of storage and use in formulation of infant food.

Preparation of Infant Formula

Once the genetically engineered human alpha-lactalbumin and beta-casein have been separated and purified, they are combined in a human infant formula. The formulation of infant formula based on bovine alpha-lactalbumin and casein has been defined. (V. S. Packard. "Human Milk and Infant Formula" pp. 147–154. Academic Press (1982)). It is suggested that the whey proteins and caseins be in a ratio of 60:40 or 0.9 weight percent alpha-lactalbumin to 0.6 weight percent casein for a total of 1.5 g protein/100 ml of milk. However, computer optimization of this ratio for the human proteins, to obtain amounts of each amino acid corresponding to the amounts actually found in human milk requires a ratio of 40:50 or 0.67 weight percent alpha-lactalbumin to 0.83 weight percent beta-casein (a total of 1.5 g protein/100 ml of milk) to reach known levels of all the essential amino acids. Supplementary amino acids, such as L-methionine used in soy-based formulas, are not needed.

Calcium is preferably of a chemical form that is biologically compatible and commercially available, such as from SIGMA Chemical Co., and should be preferably present to a minimum of 50 mg/100 kcal. Minimum phosphorus level is 25 mg/100 kcal. Minimum and maximum amounts of sodium, potassium, and chloride must also be observed. These levels are met within the ranges 6–17, 14–34, and 11–29 milliequivalents (mEq), respectively, in a formula providing 670 kcal/liter. One milliequivalent is equal to the atomic weight (in milligrams) of the element divided by valence. Osmolarity—in moles of solute/liter—should not exceed 400 mOsm.

Caloric density of infant formulas of 670 kcal/liter appears nearly optimal for normal full-term infants. The formulation should provide a calcium-phosphorus ratio preferably of not less than 1.1:1.0 nor more than 2:1. Most preferably, the ratio is near 1.5:1, at least through most of the first year of life. By one year of age, the appropriate ratio is more nearly 1:1.

Infant formulas can vary in composition, but within fairly narrow and quite precise limits. In general, as a complete substitute for human milk, formula is preferably comprised of protein at 7–16% of calories, with a preferable ratio of alpha-lactalbumin to beta-casein ranging from about 70:30 to about 30:70, fat at 30–54% of calories, linoleic acid at 2–3% of calories, and the remaining calories from carbohydrate sources. The fat component of the formula preferably comprised of various vegetable fats. Because many contaminants or pollutants of food are soluble in fat, specially refined vegetable fats and oils provide better control of formula contents. To prevent conversion of cis to trans fatty acids, and loss thereby of essential fatty acids, low- (or ultra-high) temperature treatment is preferably used throughout processing.

A representative list of ingredients follows:

Water
Lactose (Corn Syrup or Sucrose could be used)
Human Alpha-Lactalbumin
Human Beta-Casein
Coconut Oil
Soybean Oil
Modified Corn Starch
Mono- and Diglycerides
Soy Lecithin
Carrageenan Vitamin Sources Vitamin A Palmitate
Vitamin D3
Alphatocopheryl Acetate (Vitamin E)
Phytonadione (Vitamin K)
Ascorbic Acid (Vitamin C)
Thiamine Chloride Hydrochloride (Vitamin B1)
Riboflavin
Cyanocobalamin (Vitamin B12)
Niacinamide
Calcium Pantothenate
Pyridoxine Hydrochloride (Vitamin B6)
Biotin
Folic Acid
Choline Chloride Mineral Sources Calcium Phosphate, Tribasic
Cupric Sulfate
Ferrous Sulfate
Magnesium Chloride
Potassium Chloride
Potassium Citrate
Potassium Iodide
Zinc Sulfate The amounts of each of the ingredients listed are adjusted to keep each nutritional component within the maximum and minimum guidelines recommended by the FDA (V. S. Packard. "Human Milk and Infant Formula" pp. 147–154. Academic Press (1982)) and by the American Academy of Pediatrics, (Am. Acad. of Pediatrics Comm. on Nutrition, *Pediatrics*, 72, 359–363 (1983)), as disclosed below (modified from American Academy of Pediatrics, Committee on Nutrition: Commentary on Breast-Feeding and Infant Formulas, including proposed standards for formulas. *Pediatrics*, 57, 278 (1976):

Nutrient Levels of Infant Formulas (per 100 kcal) (adapted from: Anderson, S. A., H. I. Chinn, and K. D. Fisher. A background paper on infant formulas, Life Sciences Research Office, Federation of American Societies for Experimental Biology, Bethesda, Md., (1980))

| Nutrient | Minimum | Maximum |
| --- | --- | --- |
| Protein (g) | 1.8 | 4.5 |
| Fat | | |
| (g) | 3.3 | 6.0 |
| (% cal) | 30.0 | 54.0 |
| Essential fatty acids (linoleate) | | |
| (% cal) | 3.0 | — |
| (mg) | 300.0 | — |
| Vitamins | | |
| A (IU) | 250.0 (75 µg) | 750.0 (225 µg) (Retinol equivalents) |
| D (IU) | 40.0 | 100.0 |
| K (µg) | 4.0 | — |
| E (IU) | 0.3 (with 0.7 IU/g lineic acid) | — |
| C (ascorbic acid) (mg) | 8.0 | — |
| B$_1$ (thiamine) (µg) | 40.0 | — |
| B$_2$ (riboflavin) (µg) | 60.0 | — |
| B$_6$ (pyridoxine) (µg) | 35.0 (with 15 µ/g of protein in formula) | — |
| B$_{12}$ (µg) | 0.15 | — |
| Niacin | | |
| (µg) | 250.0 | — |
| (µg equiv) | — | — |
| Folic acid (µg) | 4.0 | — |
| Pantothenic acid (µg) | 300.0 | — |
| Biotin (µg) | 1.5 | — |
| Choline (mg) | 7.0 | — |
| Inositol (mg) | — | |
| Minerals | | |
| Calcium (mg) | 40.0 | — |
| Phsophorus (mg) | 25.0 | — |
| (Calcium to phosphorus ratio must be no less than 1.1 to 1.0 nor more than 2.0 to 1.0) | | |
| Magnesium (mg) | 6.0 | — |
| Iron (mg) | 0.15 | — |
| Iodine (µg) | 5.0 | — |
| ZInc (mg) | 0.5 | — |
| Copper (µg) | 60.0 | — |
| Manganese (µg) | 5.0 | — |
| Sodium (mg) | 20.0 (mEq) | 60.0 (17 mEq) |
| Potassium (mg) | 80.0 (14 mEq) | 200.0 (34 mEq) |
| Chloride (mg) | 55.0 (11 mEq) | 150.0 (29 mEq) |
| (Milliequivalents for 670 kcal/liter of formula) | | |

Carbohydrate sources include lactose (or milk and whey products that contain lactose), sucrose, corn syrup solids(a source of glucose), and starch.

Appropriate thickening agents, emulsifiers, antioxidants, and compounds for adjusting pH may be used. In the United States, conditions of use of additives in infant formula are regulated under the *Code of Federal Regulations* (CFR), Title 21, Section 172.620 and Section 180.

Vitamin additives for use in infant formulas are approved by the Food and Agricultural Organization (FAO). Processing requirements, availability, and/or stability in the specific food system will dictate which forms) will serve best.

The FAO also approves mineral sources for infant formula. Suitability of any given mineral additive depends on composition and moisture level of the food product. Furthermore, each food imposes its own requirements for flavor and/or textural stability. Oxidative rancidity is an ever-present problem in iron and/or copper-fortified foods containing unsaturated fats. Gelation is a potential problem. in concentrated liquid infant formulas. Reduced iron or electrolytic iron, which serve well in dry foods, will settle out as a sediment in liquid formula. FAO also recognizes the need for acids and bases for making pH adjustments; however, these must be accounted for in determining total content of any given mineral.

Certain mineral compounds, for instance, calcium and phosphorus, are required in fairly large amounts in infant formula. Other mineral elements are required only in trace amounts. Thus, trace minerals in ingredients of infant formula must be considered, along with those that may be added in water supplies used to reconstitute various dry ingredients. Water supplies may or may not be treated for this purpose, depending upon the overall quality. Water quality should be monitored, however, along with the trace mineral content of finished formula.

When trace minerals are added to formula, sulfate salts are commonly used. Acceptable levels of sulfate ions, however, have not been specified (Anderson, et al. (1980)). Because of the potential to cause methemoglobinemia, nitrate salts are usually not added to formula. A trace amount may occur in formula made up of vegetable products. Nitrates also occur and are occasionally found at high levels in some water supplies. Copper is another potentially toxic component of water. However, any biologically acceptable salt composition is contemplated for use in the present invention.

Minerals commonly added to formulas include calcium, phosphorus, magnesium, iron, copper, iodine, zinc, potassium, sodium, manganese, and chlorine (as chloride). Conventional infant formula compositions require the addition of bovine or soy protein sources which may have a significant amount of minerals carried along with the protein component. The presence of these minerals decreases the accuracy of determining the mineral components of the manufactured infant formula. Conventional methodologies, including electrodialysis, ion exchange and ultrafiltration, are commonly used to separate the proteins from the minerals and other contaminants associated with them. Use of the recombinant DNA-derived human proteins of the present invention in human infant formula reduce the amount protein purification necessary, thus providing a more accurate determination of mineral content and reduced expenditures for protein processing.

Formulations for Premature Infants

For preterm or low-weight infants (under 2500 g), formulas are usually modified, with the evaluation of protein and mineral levels. Lactose level may preferably be lowered by one-third to one-half regular amounts, with the difference made up with more readily absorbable carbohydrate source such as corn syrup solids. Fat, calcium, and phosphorus must be available in readily utilizable form.

Caloric density is preferably raised to 800–1000 kcal/liter; with approximately 11% of the calories from protein and 50% from fat. In general, corn and soy oil appear reasonably well absorbed by premature infants.

While particular embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

I claim:

1. A method for producing a human infant formula, comprising combining recombinant human α-lactalbumin, recombinant human β-casein, or both, with lipids from non-human sources, vitamins, minerals, and other nutrients which in combination are sufficient to meet the nutritional requirements of a human infant.

2. The method of claim 1, wherein said recombinant human α-lactalbumin is combined with said lipids, vitamins, minerals and other nutrients.

3. The method of claim 1, wherein said recombinant human β-casein is combined with said lipids, vitamins, minerals and other nutrients.

4. In a method for meeting the nutritional needs of a human infant, in which the infant is fed milk protein, vitamins, minerals, and lipids, the improvement comprising feeding the infant a recombinant human milk protein.

5. The method of claim 4, wherein said recombinant human milk protein is α-lactalbumin.

6. The method of claim 4, wherein said recombinant human milk protein is β-casein.

7. A method for producing a human infant formula, said formula comprising human α-lactaitumin or recombinant human β-casein, lipids derived from a non-human source, vitamins and minerals sufficient to meet the nutritional requirements of a human infant, comprising:

inserting at least one promoted, heterologous, expressible recombinant DNA segment encoding said human α-lactalbumin or human β-casein into a vector to produce a transforming vector;

transforming a microorganism with said transforming vector;

obtaining expression of said human α-lactalbumin or human β-casein by said transformed microorganism;

harvesting and purifying said human α-lactalbumin or human β-casein expressed by said microorganism; and formulating said human infant formula with said human α-lactalbumin or human β-casein.

8. The method of claim 7, wherein said obtaining step comprises obtaining secretion of said human α-lactalbumin or human β-casein.

9. A human infant formiula comprising protein, lipids from non-human sources, vitamins and minerals, wherein said protein comprises a recombinant human milk protein produced by a non-human organmism.

10. The infant formula of claim 9, wherein said recombinant human milk protein is human β-casein.

11. The infant formula of claim 9, wherein said recombinant human milk protein is human α-lactalbumin.

\* \* \* \* \*

UNITED STATES PATENT AND TRADEMARK OFFICE
CERTIFICATE OF CORRECTION

PATENT NO. : 5,942,274
DATED : August 24, 1999
INVENTOR(S) : Slattery

It is certified that error appears in the above-identified patent and that said Letters Patent is hereby corrected as shown below:

Column 15, Line 16 after "human" change "α-lactaitumin" to --α-lactalbumin--.

Column 16, Line 14 after "infant" change "formiula" to --formula--.

Column 16, Line 17 after "non-human" change "organmism" to --organism--.

Signed and Sealed this

Eighteenth Day of July, 2000

*Attest:*

Q. TODD DICKINSON

*Attesting Officer*     *Director of Patents and Trademarks*